(12) United States Patent
Brandl et al.

(10) Patent No.: US 7,108,658 B2
(45) Date of Patent: Sep. 19, 2006

(54) METHOD AND APPARATUS FOR C-PLANE VOLUME COMPOUND IMAGING

(75) Inventors: Helmut Brandl, Pfaffing (AT); Harald Deischinger, Frankenmarkt (AT)

(73) Assignee: General Electric Company, Schenectady, NY (US)

( * ) Notice: Subject to any disclaimer, the term of this patent is extended or adjusted under 35 U.S.C. 154(b) by 101 days.

(21) Appl. No.: 10/652,917

(22) Filed: Aug. 29, 2003

(65) Prior Publication Data

US 2005/0049479 A1  Mar. 3, 2005

(51) Int. Cl.
*A61B 8/00* (2006.01)
(52) U.S. Cl. ..................... 600/443; 128/916
(58) Field of Classification Search ........ 600/440–447; 73/625–626; 128/916
See application file for complete search history.

(56) References Cited

U.S. PATENT DOCUMENTS

| | | | |
|---|---|---|---|
| 5,454,371 A * | 10/1995 | Fenster et al. | 600/443 |
| 5,546,807 A * | 8/1996 | Oxaal et al. | 73/606 |
| 5,787,889 A | 8/1998 | Edwards et al. | |
| 5,911,691 A | 6/1999 | Mochizuki et al. | |
| 5,931,784 A * | 8/1999 | Kajiwara et al. | 600/441 |
| 5,986,662 A * | 11/1999 | Argiro et al. | 345/424 |
| 6,106,471 A | 8/2000 | Wiesauer et al. | |
| 6,186,949 B1 | 2/2001 | Hatfield et al. | |
| 6,201,900 B1 | 3/2001 | Hossack et al. | |
| 6,213,947 B1 | 4/2001 | Phillips | |
| 6,254,540 B1 | 7/2001 | Kikuchi et al. | |
| 6,283,918 B1 | 9/2001 | Kanda et al. | |
| 6,450,962 B1 | 9/2002 | Brandl et al. | |
| 6,544,178 B1 * | 4/2003 | Grenon et al. | 600/443 |
| 6,692,441 B1 * | 2/2004 | Poland et al. | 600/443 |

OTHER PUBLICATIONS

Karl Heinz Höhne, Michael Bamans, Andreas Pommert, Martin Riemer, Ulf Tiede, Gunnar Wiebecke, Rendering Tomographic Volume Data: Adequacy of Methods for Different Modalities and Organs, A Survey of 3D Display Techniques to Render Medical Data, published in 3D Imaging in Medicine: Algorithms, Systems, Applications, Karl Heinz Hohne et al. editors, Springer-Verlag, Berlin Heidelberg, NATO ASI Series F: Computer and Systems Sciences, vol. 60, pp. 175-195 (1990).

Jean-Louis Coatrieux, Christian Barillot, A Survey of 3D Display Techniques to Render Medical Data, published in 3D Imaging in Medicine: Algorithms, Systems, Applications, Karl Heinz Hohne et al. editors, Springer-Verlag, Berlin Heidelberg, NATO ASI Series F: Computer and Systems Sciences, vol. 60, pp. 175-195 (1990).

* cited by examiner

Primary Examiner—Francis J. Jaworski
(74) Attorney, Agent, or Firm—Carl B. Horton, Esq.; Armstrong Teasdale LLP

(57) ABSTRACT

Method and apparatus for displaying an enhanced image based on an image plane of data. A volume data set is acquired, and a plane is defined on an image based on the volume data set. The plane may be a C-plane. Data within the volume data set which is defined by the plane is processed with an image enhancing technique and the resultant enhanced image is displayed.

21 Claims, 6 Drawing Sheets

METHOD AND APPARATUS FOR C-PLANE VOLUME COMPOUND IMAGING

BACKGROUND OF THE INVENTION

This invention relates generally to diagnostic ultrasound systems. In particular, the present invention relates to method and apparatus for processing and displaying an enhanced image based on an identified plane within a volume of data.

Conventional ultrasound scanners are capable of acquiring and displaying a volume of data. Unfortunately, it has been difficult to correctly identify a specific plane of data within the volume of data that a user wishes to see. It has been necessary in conventional ultrasound scanners to store the volume of data prior to processing in order to locate the desired anatomic data. Unfortunately, this is time consuming and may result in longer exam times to acquire and process additional data, and may perhaps require additional volumes of data to be acquired or an exam to be repeated.

Additionally, there is a need to correlate the resultant processed image with its location within the volume of data. It may be desirable to view data which is near the identified plane but not currently selected. Also, it may be desirable to view data near or in the identified plane in a different manner, such as by enhancing different features. The features may be bone or soft tissue, for example. Furthermore, doctors who may be more familiar with reviewing image data from other modalities, such as X-ray, may find reviewing the ultrasound data more valuable if X-ray-like images could be created from the ultrasound volume for comparison with the volume of data.

Thus, a system and method are desired to process and display data from within a volume that addresses the problems noted above and others previously experienced.

BRIEF DESCRIPTION OF THE INVENTION

In one embodiment, a method for displaying an enhanced C-plane image comprises acquiring a volume data set. A C-plane is defined on a first image. The first image is based on the volume data set. An enhanced image is displayed based on the C-plane.

In one embodiment, a method for displaying an enhanced image comprises acquiring a volume data set. A B-mode image is displayed based on the volume data set. A plane is identified within the B-mode image. A portion of the volume data set based on the plane is processed with an image enhancing technique. An enhanced image is displayed based on the plane.

In one embodiment, a system for displaying an image enhanced plane of data comprises a transducer for transmitting and receiving ultrasound signals to and from an area of interest. A receiver receives the ultrasound signals which comprise a series of adjacent scan planes comprising a volumetric data set. The system includes an input for defining a plane within the volumetric data set. The plane identifies a subset of the volumetric data set. A processor processes the subset with an image enhancing technique and creates an enhanced image. An output presents the enhanced image.

DETAILED DESCRIPTION OF THE INVENTION

Figure 1:
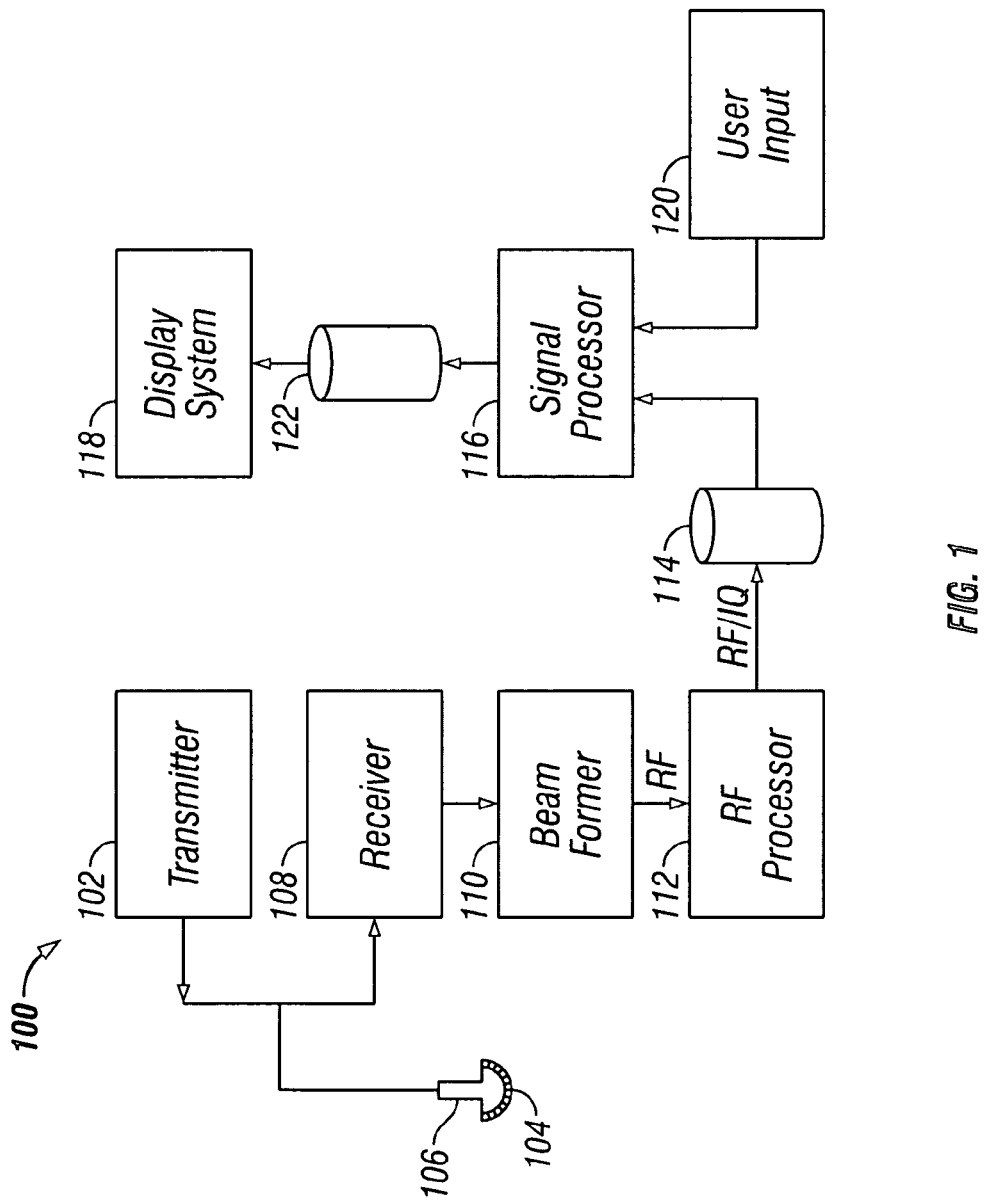
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives transducers 104 within a transducer 106 to emit pulsed ultrasonic signals into a body. A variety of geometries may be used. The ultrasonic signals are back-scattered from structures in the body, like blood cells or muscular tissue, to produce echoes which return to the transducer elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage. A user input 120 may be used to input patient data, scan parameters, a change of scan mode, and the like.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
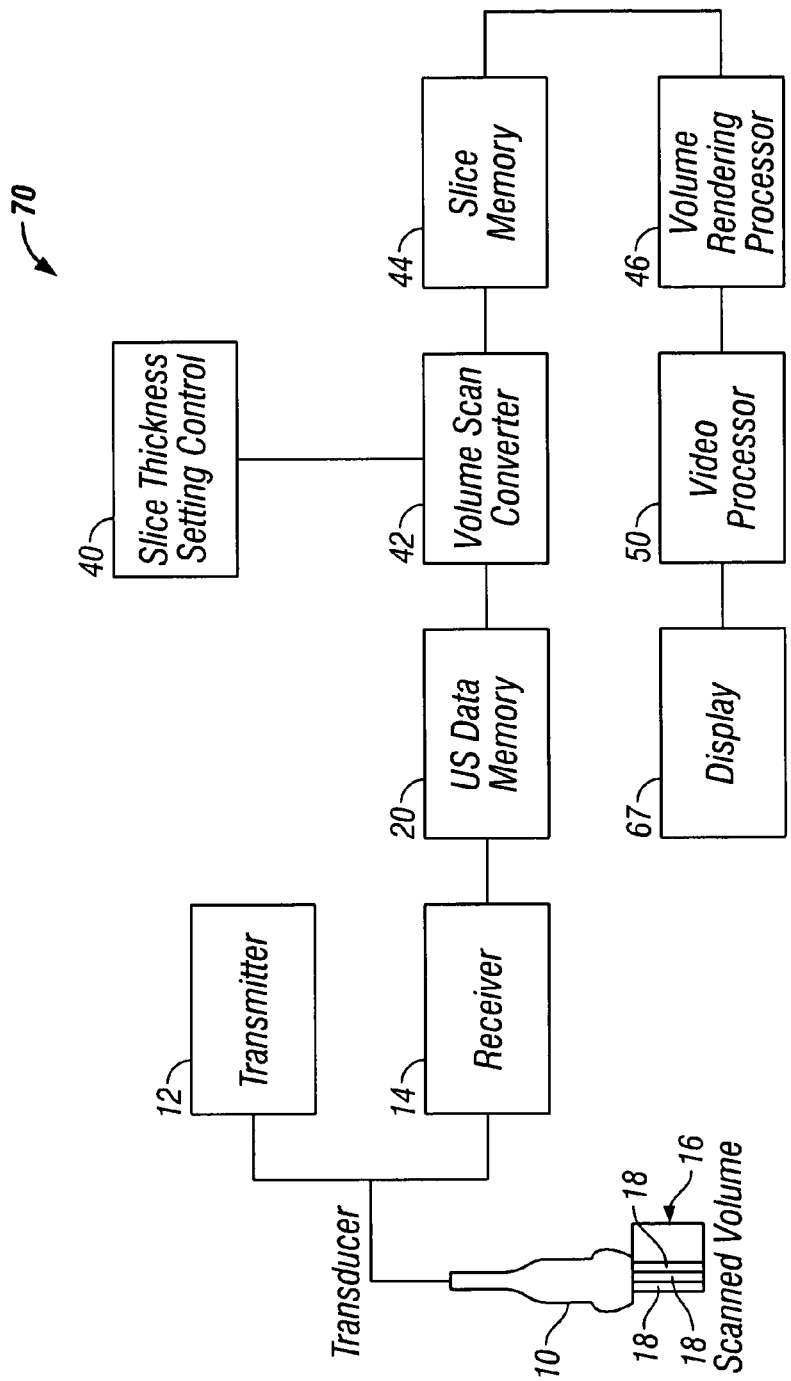
FIG. 2 illustrates an ultrasound system formed in accordance with an embodiment of the present invention.

FIG. 2 illustrates an ultrasound system 70 formed in accordance with one embodiment of the present invention. The system 70 includes a transducer 10 connected to a transmitter 12 and a receiver 14. The transducer 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains scan planes 18. The scan planes 18 are collected for a thickness, such as from a group or set of adjacent scan planes 18. The scan planes 18 are stored in the memory 20, and then passed to a volume scan converter 42. In some embodiments, the transducer 10 may obtain lines instead of the scan planes 18, and the memory 20 may store lines obtained by the transducer 10 rather than the scan planes 18. The volume scan converter 42 may store lines obtained by the transducer 10 rather than the scan planes 18. The volume scan converter 42 receives a slice thickness setting from a control input 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by slice thickness control input 40. The data slice is stored in slice memory 44 and is accessed by a volume rendering processor 46. The volume rendering processor 46 performs volume rendering upon the data slice. The output of the volume rendering processor 46 is passed to the video processor 50 and display 67.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

Figure 3:
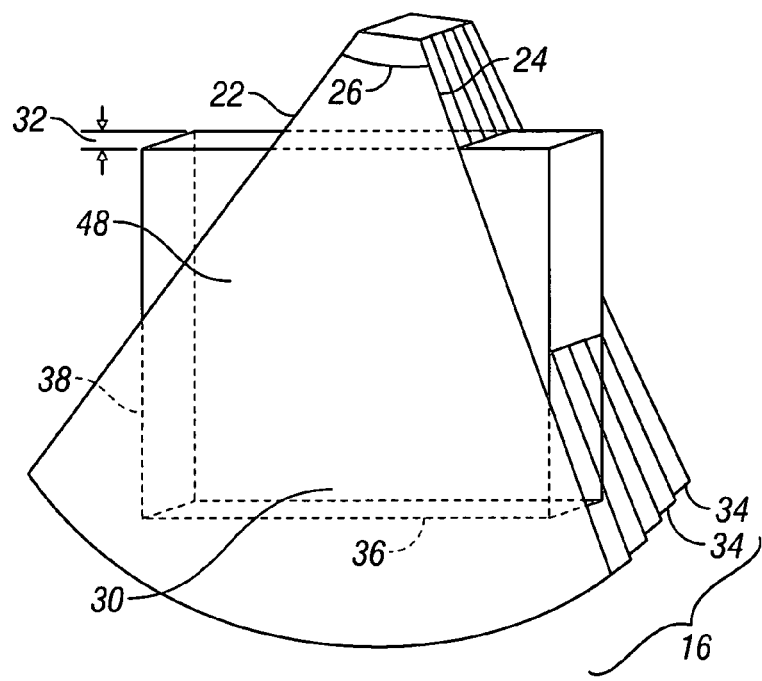
FIG. 3 illustrates a real-time 4D volume acquired by the system of FIG. 2 in accordance with an embodiment of the present invention.

FIG. 3 illustrates a real-time 4D volume 16 acquired by the system 70 of FIG. 2 in accordance with one embodiment. The volume 16 includes a sector shaped cross-section with radial borders 22 and 24 diverging from one another at angle 26. The transducer 10 electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the transducer 10, as illustrated in FIG. 2, are stored in memory 20 and are scan converted from spherical to Cartesian coordinates by the volume scan converter 42. A volume comprising multiple scan planes is output from the volume scan converter 42 and stored in the slice memory 44 as rendering box 30. The rendering box 30 in the slice memory 44 is formed from multiple adjacent image planes 34.

The rendering box 30 may be defined in size by an operator to have a slice thickness 32, width 36 and height 38. The volume scan converter 42 may be controlled by the slice thickness control input 40 to adjust the thickness parameter of the slice to form a rendering box 30 of the desired thickness. The rendering box 30 designates the portion of the scanned volume 16 that is volume rendered. The volume rendered processor 46 accesses the slice memory 44 and renders along the thickness 32 of the rendering box 30.

During operation, a 3D slice having a pre-defined, substantially constant thickness (also referred to as the rendering box 30) is acquired by the slice thickness setting control 40 (FIG. 2) and is processed in the volume scan converter 42 (FIG. 2). The echo data representing the rendering box 30 may be stored in slice memory 44. Predefined thicknesses between 2 mm and 20 mm are typical, however, thicknesses less than 2 mm or greater than 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image plane 34 (FIG. 3). Following processing in the volume rendering processor 46, the pixel data in the image portion 48 may pass through a video processor 50 and then to a display 67. The rendering box 30 may be located at any position and oriented at any direction within the scanned volume 16. In some situations, depending on the size of the region being scanned, it may be advantageous for the rendering box 30 to be only a small portion of the scanned volume 16.

Figure 4:
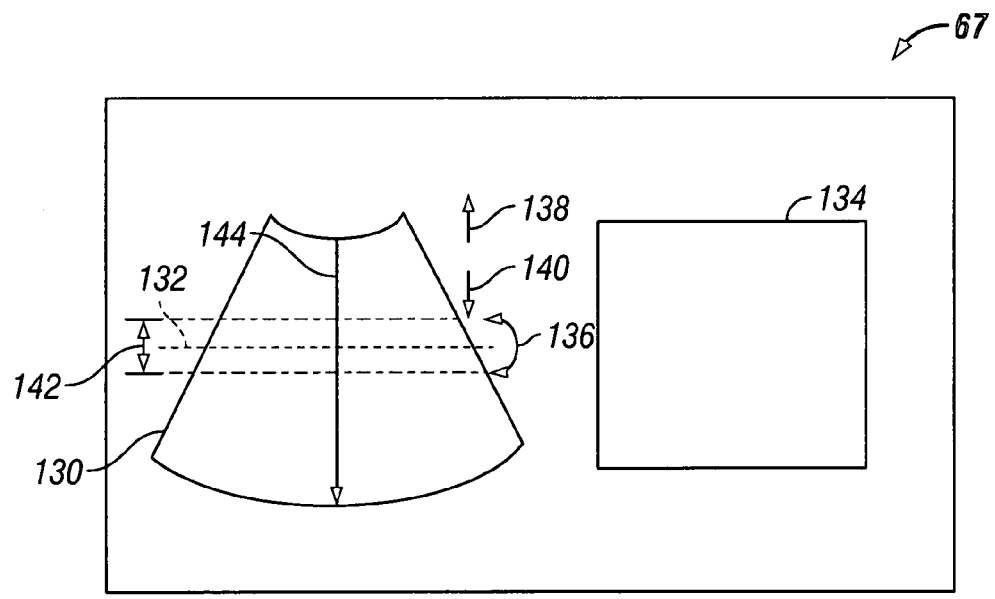
FIG. 4 illustrates a B-mode image and an enhanced image on the display in accordance with an embodiment of the present invention.

FIG. 4 illustrates a B-mode image 130 having a depth 144 to one side of the display 67. Although the image being displayed is a B-mode image, a volume data set, such as volume 16 of adjacent image planes 34 (FIG. 3), has been acquired in real-time as discussed previously. A user may use the user input 120 to define a plane 132 of interest on the B-mode image 130. The plane 132 identifies a plane, such as the C-plane (i.e. anterior-to-posterior) through the volume data set having a minimum thickness of 0.1 mm. Therefore, the plane 132 defines a portion, or subset, of the data set or volume 16. The plane 132 may be radial, perpendicular, or at an intermediate angle with respect to the transducer 10. Once the plane 132 has been identified, the user may rotate the plane 132 through an angle 136 with the user input 120. The user may also move the plane 132 up 138 towards the transducer 10 or down 140 away from the transducer 10.

The user may then select an image enhancement technique and/or other processing to be done to the volume data set identified by the plane 132. The image enhancement technique may be a volume rendering technique, for example. The user may wish to display image data associated with bone, and therefore selects an image enhancement technique based on this anatomic feature. Other anatomic features such as soft tissue and vessels may also be processed. For example, the user may use the user input 120 to select a volume rendering technique such as maximum density to display an enhanced image of bone. Alternatively, a subset of image enhancement techniques may be offered or suggested to the user based on the type of scan being performed, such as fetal scan, liver, and the like. The data set identified by the plane 132 is processed to create an enhanced image 134. The enhanced image 134 may be displayed in real-time on display 67 alone, such as in a larger format than illustrated in FIG. 4. Alternatively, the enhanced image 134 may be displayed on the display 67 simultaneously and in real-time with the B-mode image 130.

Additionally, the user may modify a thickness 142 of the volume data set. For example, the thickness 142 may be equidistant above and below the plane 132, or the plane 132 may identify the top or bottom of the thickness 142. The thickness 142 may or may not be displayed on display 67 as lines or in numerical format (not shown). In other words, varying the thickness 142 allows the user to view image data from multiple layers of the volume 16 that are parallel to the C-plane, or other plane 132, that the user has defined. The thickness 142 defined may be based on the image enhancement technique, the anatomic feature, the depth 144, and/or the acquisition type. If the user changes the position of the plane 132 after modifying the thickness 142, the size of the thickness 142 may be maintained. For example, if the user wishes to display an enhanced image 134 based on bone, a thicker thickness 142 is defined. If the user wishes to display an enhanced image 134 based on vessels, a thinner thickness 142 is defined.

Changes made by the user to the position of the plane 132 and the thickness 142 may be displayed in real-time. Therefore, the enhanced image 134 is updated as the plane 132 and/or thickness 142 are varied. Therefore, a user may continue to modify the thickness 142 and move the plane 132 until the desired enhanced image 134 is displayed.

Figure 5:
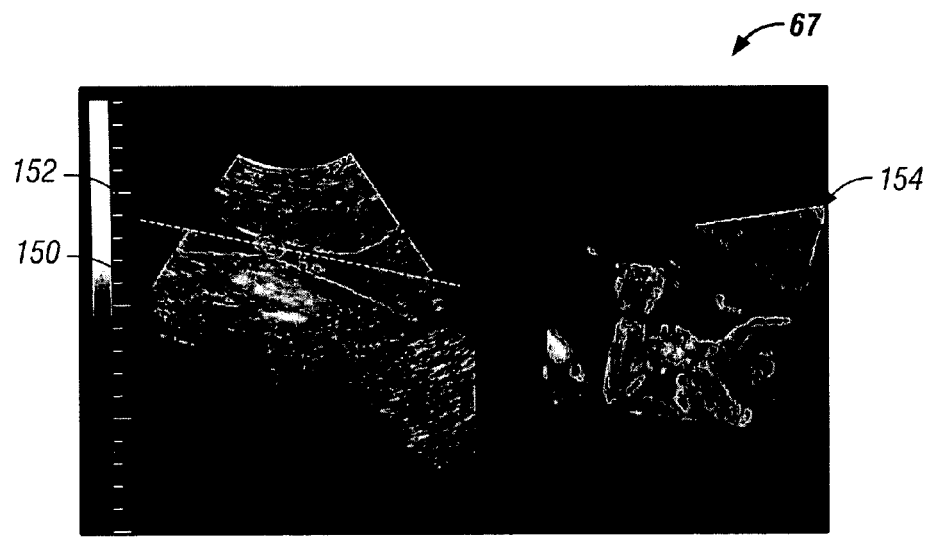
FIG. 5 illustrates a B-mode image with a plane of interest identified in accordance with an embodiment of the present invention.

FIG. 5 illustrates a B-mode image 150 with plane 152 identifying a plane of interest. The plane 152 may define the C-plane as previously discussed. The B-mode image 150 provides a frame of reference for the user, allowing the user to identify the plane 152 based on real-time data. By way of example only, the B-mode image 150 in FIG. 5 illustrates a fetus. It should be understood that other anatomy may be scanned and processed, such as the liver, heart, kidneys, and the like.

An enhanced image 154 corresponding to the plane 152 is illustrated simultaneously on the display 67 with the B-mode image 150. In this example, the user has selected the plane 152 to display a C-plane image of the fetal arms using a volume contrast imaging technique, such as maximum density. The size of the thickness 142 may be increased or decreased as discussed previously.

Figure 6:
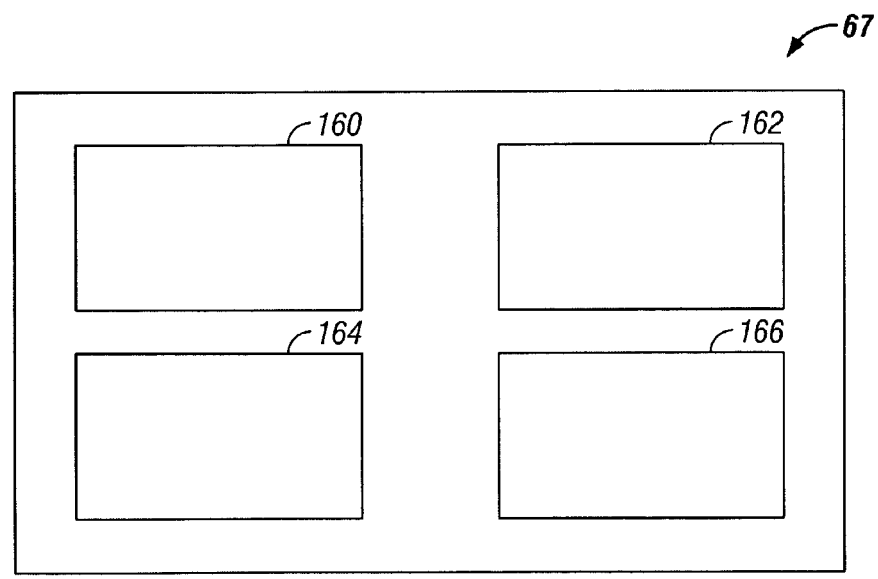
FIG. 6 illustrates four enhanced images displayed simultaneously on the display in accordance with an embodiment of the present invention.

FIG. 6 illustrates four enhanced images 160–166 displayed simultaneously on the display 67. Each of the enhanced images 160–166 have been processed according to a predefined set of image enhancing techniques, and correspond to a plane of data, such as the plane 132 of FIG. 4.

Figure 8:
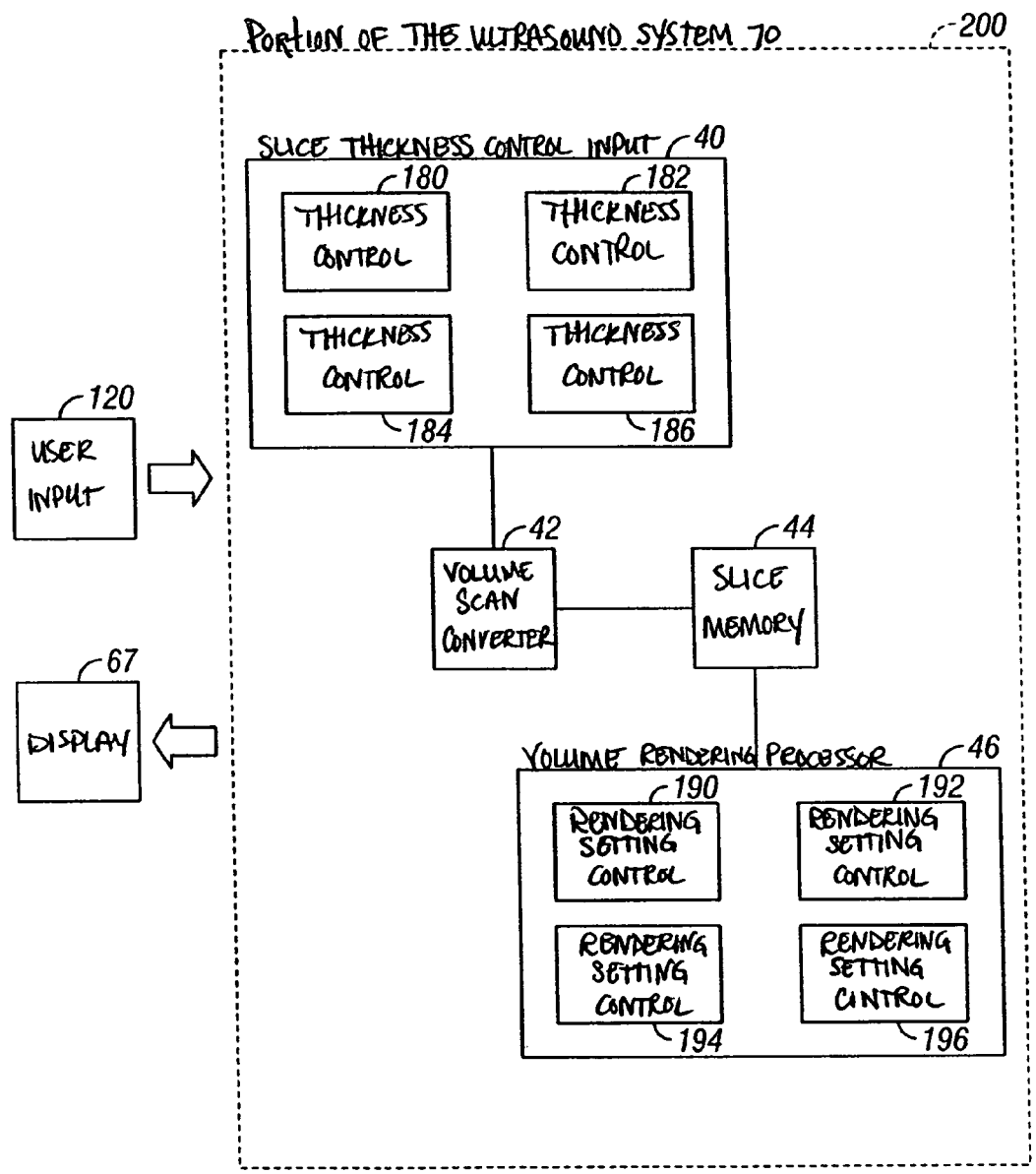
FIG. 8 illustrates a block diagram of a portion of the ultrasound system of FIG. 2 in accordance with an embodiment of the present invention.

FIG. 8 illustrates a block diagram of a portion 200 of the ultrasound system 70 of FIG. 2. In FIG. 8, the slice thickness setting control 40 includes four individual thickness controls 180–186. The volume rendering processor 46 includes four individual rendering setting controls 190–196. It should be understood that FIG. 8 is a conceptual representation only. For example, a single slice thickness setting control 40 may be used to set multiple different slice thicknesses 142 simultaneously, and a single volume rendering processor 46 may be used to set the different rendering techniques and process multiple volumes of data simultaneously.

When the user begins to acquire the B-mode volume data set, the type of scan being performed, such as of a fetus, a liver, and the like, is identified through the user input 120. The user also adjusts the depth 144 of the scan to include the desired information within the B-mode image. The operator then defines the plane 132, as discussed previously with FIG. 4. Although the following discussion is limited to acquiring 3-D and 4-D B-mode volumetric data, it should be understood that other acquisition modes may be used, such as conventional grayscale sonography, B-flow, harmonic and co-harmonic sonography, color Doppler, tissue harmonic imaging, pulse inversion harmonic imaging, Power Doppler, and tissue Doppler.

Depending upon the acquisition type, a different subset of anatomic features, associated with a different subset of image enhancing techniques, may be expected. For example, when scanning a fetus, the subset of anatomic features may include bone, vessel, contrast, and soft tissue, which have known ultrasound characteristic responses. When scanning a liver, however, the system 70 may not include bone in the subset of anatomic features. In addition, the depth 144 of the scan also impacts the thickness 142 which is associated with the image enhancing techniques.

The user may then initiate the automatic processing of the four enhanced images 160–166 through the user input 120. For example, the user input 120 may comprise a single protocol or button selection. A subset of anatomic features having associated image enhancing techniques has been predefined. The subset may provide a default, which is applied when scanning any anatomy. Alternatively, the subset of anatomic features may be based on one or more of the type of acquisition, probe type, the depth 144, and the like. The thickness controls 180–186 of the slice thickness setting control 40 automatically set the predefined subset of anatomic features. Therefore, each of the thicknesses 142 for the different enhanced images 160–166 include at least a common subset of the data set. The rendering setting controls 190–196 of the volume rendering processor 46 automatically identify the appropriate image enhancing techniques, and the volume rendering processor 46 processes the slice data identified by the respective thickness controls 180–186. The enhanced images 160–166 are then displayed on display 67. Therefore, the correct thickness 142 of each enhanced image 160–166 is automatically defined for the user, so there is no need for the user to manually vary the thickness 142 to display enhanced images of different anatomic features.

For example, enhanced image 160 may use a "bone" anatomic feature setting. With this setting, the thickness control 180 automatically defines the thickness 142, such as between 10–15 mm. The rendering setting control 190 identifies the correct technique, such as a maximum density rendering technique, and the volume rendering processor 46 processes the layers of the volume 16 that are parallel to the plane 132 and within the thickness 142. Enhanced image 162 may use a "soft tissue" anatomic feature setting. With this setting, the thickness control 182 identifies the thickness 142, which may be approximately 3 mm. The rendering setting control 192 identifies the correct technique, such as an X-ray rendering technique, and the volume rendering processor 46 processes the layers of the volume 16 that are parallel to the plane 132 and within the thickness 142. The X-ray rendering technique may be used to provide an image comparable to an slice image created when using X-ray radiation. This technique may also be called average projection. Other rendering modes may be used to enhance anatomic features, such as gradient light rendering and maximum transparency. Additionally, other image processing techniques may be used to process and create enhanced images.

Similarly, enhanced images 164 and 166 may use "contrast" and "vessels" anatomic feature settings, respectively. The thickness controls 184 and 186 identify the thicknesses 142 (by way of example only, 1 mm with threshold low 0, and 5–10 mm, respectively) and the rendering setting controls 194 and 196 identify the techniques (by way of example only, surface and minimum density rendering techniques, respectively). The volume rendering processor 46 processes the layers of the volume 16 that are parallel to the plane 132 and within the thicknesses 142 for each of the enhanced images 164 and 166.

The enhanced images 160–166 are displayed simultaneously on display 67. It should be understood that although the aforementioned process was discussed as creating the enhanced images 160–166 singularly, the enhanced images 160–166 may be created at the same time. Therefore, multiple anatomic features may be enhanced and displayed on the display 67, and be contrasted with respect to each other at the same time.

Therefore, the displaying and processing of the volume data set is automatically performed by predefining the subset of anatomic features within the volume data set to be processed, and identifying the associated subset of image enhancing techniques. The user does not have to choose the correct image enhancing technique nor define the correct thickness 142 for the scan to display the desired enhanced image 160–166 of an anatomic feature. Additionally, by automatically displaying multiple enhanced images 160–166 based on the same C-plane volume data set, where the enhanced images 160–166 include at least a common subset of the data set, the images comprising different anatomic features of the same plane 132 (C-plane) may be easily compared. Thus, by presenting the processed information automatically, it is less likely that valuable diagnostic data may not be displayed or may be overlooked. Also, the user input, such as the number of key strokes and other required entries, is greatly simplified, and the time required to manually process the enhanced images 160–166 is eliminated.

Alternatively, the user may predefine the different anatomic features they wish to have automatically identified and processed. The user's predefined subset of anatomic features and the associated image enhancing techniques may be based on the acquisition type, probe type, and/or personal preference and the like. It should be understood that although four enhanced images 160–166 are illustrated in FIG. 6, more or less enhanced images 160–166 may be displayed based on the size of the display 67, user preference, and the like.

Figure 7:
FIG. 7 illustrates multiple enhanced images based on the C-plane identified by the plane of FIG. 5 in accordance with an embodiment of the present invention.

FIG. 7 illustrates multiple enhanced images 172–178 based on a C-plane, such as the C-plane identified by plane 152 of FIG. 5. After the user identifies the type of scan and plane 152, enhanced images 172–178 are automatically processed and displayed. Enhanced image 172 is processed using the bone anatomic feature setting, or the maximum density rendering technique. Enhanced image 174 is processed using the soft tissue anatomic feature setting, or the X-ray rendering technique. Enhanced image 176 is processed using the contrast anatomic feature setting, or the surface rendering technique. Enhanced image 178 is processed using the vessels anatomic feature setting, and the minimum density rendering technique. The enhanced images 172–178 are displayed simultaneously on display 67.

The enhanced images 172–178 may be displayed in real-time as the volume 16 is being acquired. In this embodiment, the B-mode image 150 may be displayed on a different display 67, not displayed, or displayed in place of or in addition to, one of the enhanced images 172–178. Alternatively, the volume 30 may be acquired and stored prior to creating the enhanced images 172–178. It should be understood that although FIGS. 5 and 7 utilize volume rendering techniques as the image enhancing technique, other image enhancing techniques may be used to process enhanced images 154 and 172–178.

While the invention has been described in terms of various specific embodiments, those skilled in the art will recognize that the invention can be practiced with modification within the spirit and scope of the claims.

What is claimed is:

1. A method for processing enhanced C-plane images, comprising:

acquiring a volume data set;
defining a C-plane on a first image, said first image being based on said volume data set;
defining first and second subsets of said volume data set, said first and second subsets comprising said C-plane;
identifying first and second thicknesses of said C-plane, said first and second thicknesses identifying said first and second subsets of said volume data set, respectively, said first and second thicknesses being different with respect to each other; and
processing said first and second subsets to create enhanced images.

2. The method of claim 1, said volume data set further comprising anatomic features, said anatomic features comprising at least one of bone, soft tissue, contrast and vessels.

3. The method of claim 1, further comprising:
selecting a volume rendering technique;
said processing step further comprising processing one of said first and second subsets with said volume rendering technique; and
displaying an enhanced image based on said volume rendering technique.

4. The method of claim 1, further comprising:
said volume data set further comprising multiple anatomic features; and
selecting volume rendering techniques to enhance one of said anatomic features, said volume rendering techniques being one of surface texture, maximum density, minimum density, average projection, gradient light rendering, and maximum transparency, said enhanced image being based on said volume rendering techniques.

5. The method of claim 1, further comprising using an acquisition mode to acquire said volume data set, said acquisition mode being one of 3-D volume, 4-D volume, conventional grayscale sonography, B-flow, color Doppler, tissue Doppler, Power Doppler, and harmonic and co-harmonic sonography.

6. The method of claim 1, further comprising:
identifying an acquisition type;
presenting a subset of image enhancing techniques based on said acquisition type; and
displaying an enhanced image based on one of said image enhancing techniques and one of said first and second subsets.

7. The method of claim 1, wherein said first image being a B-mode image based on said volume data set.

8. The method of claim 1, further comprising displaying said first image and at least one said enhanced image simultaneously.

9. The method of claim 1, further comprising:
modifying a location of said C-plane in at least one of rotation angle and depth; and
displaying an updated enhanced image in real-time based on said location and at least one of said first and second subsets.

10. The method of claim 1, further comprising:
modifying at least one of said first and second thickness; and
updating an enhanced image in real-time based on a modified thickness.

11. The method of claim 1, said processing step further comprising automatically selecting first and second volume rendering techniques, said first and second volume rendering techniques enhancing first and second anatomic features, respectively, said first and second anatomic features being different with respect to each other, said first and second volume rendering techniques being different with respect to each other.

12. A method for displaying an enhanced image, comprising:
　　acquiring a volume data set;
　　displaying a B-mode image based on said volume data set;
　　identifying a plane within said B-mode image;
　　defining first and second subsets of said volume data set, said first and second subsets comprising said plane;
　　processing said first and second subsets with first and second image enhancing techniques to create first and second enhanced images, said processing automatically selecting first and second volume rendering techniques defining said first and second image enhancing techniques, said first and second volume rendering techniques enhancing first and second anatomic features, respectively, to provide said first and second enhanced images, said first and second anatomic features being different with respect to each other, said first and second volume rendering techniques being different with respect to each other; and
　　displaying said first and second enhanced images simultaneously.

13. The method of claim 12, said volume data set further comprising anatomic features, said anatomic features comprising at least one of bone, soft tissue, contrast and vessels.

14. The method of claim 12, further comprising modifying a location of said plane in at least one of rotation angle and depth, said displaying step further comprising displaying updated first and second enhanced images in real-time based on said location.

15. The method of claim 12, further comprising:
　　identifying a thickness of said first subset, said thickness comprising a subset of said volume data set, said first enhanced image being based on said first subset; and
　　modifying said thickness, said first enhanced image being updated in real-time based on a modified thickness.

16. The method of claim 12, said displaying step further comprising displaying said B-mode and said first and second enhanced images simultaneously and in real-time.

17. An apparatus for displaying an image enhanced plane of data, comprising:
　　a transducer for transmitting and receiving ultrasound signals to and from an area of interest;
　　a receiver for receiving said ultrasound signals comprising a series of adjacent scan planes comprising a volumetric data set;
　　an input for defining a plane within said volumetric data set, said plane identifying a subset of said volumetric data set;
　　a processor for identifying first and second subsets of said volumetric data set comprising said plane and for identifying first and second thicknesses of said plane, said first and second thicknesses identifying said first and second subsets of said volume data set, respectively, said first and second thicknesses being different with respect to each other, said processor processing said first and second subsets with first and second image enhancing techniques to create first and second enhanced images; and
　　an output for presenting at least one of said first and second enhanced images.

18. The apparatus of claim 17, further comprising a second input for defining at least one of said first and second thickness of said plane.

19. The apparatus of claim 17, further comprising a second input for modifying said plane, said second input moving a location of said plane in at least one of a rotation angle and a depth, said output presenting at least one updated enhanced image in real-time as said location changes.

20. The apparatus of claim 17, further comprising a second input for inputting said first and second image enhancing techniques.

21. The apparatus of claim 17, further comprising a second input for inputting an acquisition mode, said processor choosing said first and second image enhancing techniques based on said acquisition mode.

* * * * *